(12) United States Patent
Wang et al.

(10) Patent No.: US 7,648,467 B2
(45) Date of Patent: Jan. 19, 2010

(54) DEVICE FOR NON-SURGICAL CORRECTION OF CONGENITAL INVERTED NIPPLES AND/OR COLLECTION OF NIPPLE ASPIRATE FLUID

(76) Inventors: Paul C. Wang, 115 E. 9th St., #18L, New York, NY (US) 10003; Kathleen McConnell, 300 E. 33rd St., #3F, New York, NY (US) 10016

( * ) Notice: Subject to any disclaimer, the term of this patent is extended or adjusted under 35 U.S.C. 154(b) by 980 days.

(21) Appl. No.: 11/292,265

(22) Filed: Dec. 2, 2005

(65) Prior Publication Data
US 2006/0178601 A1 Aug. 10, 2006

Related U.S. Application Data

(66) Substitute for application No. 60/634,222, filed on Dec. 8, 2004.

(60) Provisional application No. 60/634,091, filed on Dec. 8, 2004.

(51) Int. Cl.
*A61B 5/00* (2006.01)
*B65D 81/00* (2006.01)

(52) U.S. Cl. .................... 600/573; 604/73; 604/74; 604/75; 604/315; 604/316

(58) Field of Classification Search .......... 600/573–583; 604/73–75, 289, 315–316
See application file for complete search history.

(56) References Cited

U.S. PATENT DOCUMENTS

| 11,623 A | 8/1854 | Waters |
| 29,662 A | 8/1860 | Beadle |
| 897,289 A | 9/1908 | Howell |
| 1,509,226 A | 9/1924 | Brown |
| 1,922,947 A | 8/1933 | Grotte |

(Continued)

FOREIGN PATENT DOCUMENTS

EP 0 442 758 8/1991

(Continued)

*Primary Examiner*—Max Hindenburg
*Assistant Examiner*—Rene Towa
(74) *Attorney, Agent, or Firm*—Antonelli, Terry, Stout & Kraus, LLP.

(57) ABSTRACT

The invention is an apparatus (10) for treating inverted nipples and/or the collection of NAF. The invention includes an assembly which creates an airtight seal upon attachment to at least an areola (16) of an inverted nipple (18) and by rotation of a part thereof draws a partial vacuum to apply an outward force to the nipple; and a syringe (26) including a curved longitudinal axis (28), the syringe being carried by the assembly and being in fluid communication with a chamber (24) of the assembly upon attachment of the assembly to at least an areola of an inverted nipple, the syringe including a plunger (30) which is sealed against an inner surface (34) of the syringe and is rotatable to move along the longitudinal axis relative to the chamber which moves the plunger within a syringe body to expel air from the syringe body away from the chamber upon rotation of the plunger in a first direction and to aspirate air from the chamber upon attachment of the apparatus to the breast surrounding the nipple upon rotation in a second direction opposite to the first direction to create a partial vacuum within the chamber to evert the nipple.

38 Claims, 7 Drawing Sheets

U.S. PATENT DOCUMENTS

| | | |
|---|---|---|
| 2,120,872 A | 6/1938 | Seward |
| 3,786,801 A | 1/1974 | Sartorius |
| 5,520,613 A | 5/1996 | Copelan |
| 5,798,266 A | 8/1998 | Quay et al. |
| 5,871,456 A | 2/1999 | Armstrong et al. |
| 5,947,923 A | 9/1999 | Uehara et al. |
| 6,010,466 A | 1/2000 | McGeorge |
| 6,210,360 B1 | 4/2001 | Kong |
| 6,287,521 B1 | 9/2001 | Quay et al. |
| 6,500,112 B1 | 12/2002 | Khouri |
| 6,689,073 B2 | 2/2004 | Quay |
| 6,712,785 B2 | 3/2004 | Morton et al. |
| 2001/0031911 A1 | 10/2001 | Khouri |
| 2002/0072702 A1 | 6/2002 | Quay |
| 2004/0176707 A1 | 9/2004 | Park |

FOREIGN PATENT DOCUMENTS

| | | |
|---|---|---|
| GB | 2 240 924 | 8/1991 |
| GB | 2 325 411 A | 11/1998 |
| WO | WO 96/29043 | 9/1996 |
| WO | WO 03/017912 A1 | 3/2003 |

DEVICE FOR NON-SURGICAL CORRECTION OF CONGENITAL INVERTED NIPPLES AND/OR COLLECTION OF NIPPLE ASPIRATE FLUID

CROSS REFERENCE TO RELATED APPLICATIONS

Reference is made to Provisional Application Ser. Nos. 60/634,091 and 60/634,222 each filed on Dec. 8, 2004, which applications are incorporated herein by reference in their entirety.

BACKGROUND OF THE INVENTION

Between 2% and 3% of women are born with one or both nipples congenitally inverted. An inverted nipple is caused when the lactiferous ducts are shorter than normal exerting traction on the center of the nipple and preventing the nipple from protruding forward of the nipple-areola complex to assume the more classic everted shape. Congenital inverted nipples are to be distinguished from the inversion of a nipple that was previously normal; such inversion can be caused by abnormal growth within the breast tissue including cancerous tumors. Congenitally inverted nipples are not thought to be susceptible to pathology but have been known to complicate breast feeding in view of it being harder to for a newborn to latch on to the nipple and therefore make breast feeding more difficult for both mother and baby. Similarly, non-lactating women may desire to correct congenitally inverted nipples for purely cosmetic reasons.

Surgical techniques exist to correct congenitally inverted nipples, but these engender all the risks and expense associated with surgery included, but not limited to infection, and complications associated with anesthesia. These surgical corrections also carry the essential added complication of interrupting normal anatomy of the lactiferous ducts rendering the ducts incapable of normal lactation.

Breast cancer is the most common cancer in women and successful treatment for breast cancer hinges primarily on the stage at which the cancer is detected. The current screening techniques, mammography and physical exam, are severely limited by their ability to detect breast pathology until the cancerous growth has reached at least one or more often two centimeters in size. Eighty to ninety percent of breast cancers arise in the intraductal epithelial cells of the breast making nipple aspirated fluid (NAF) from these ducts an ideal sample for the early detection of cancerous transformation. Such fluid yields cytology samples, as well as cell products which are subject to analysis providing an indicator of cancerous transformation of previously healthy tissue including cell proliferation markers, oncogenes, growth factors and growth factor receptors, angiogenic factors, proteases, adhesion factors and tumor suppressor genes. Research on NAF is ongoing and rapidly expanding, and the list of markers will continue to expand as well.

Numerous devices exist both for the application of a partial vacuum to an inverted nipple or the collection of NAF. Those devices which are designed for the eversion of nipples have bulky designs or structures which are complicated and/or difficult to use. Those devices for collecting NAF are used by clinicians in a clinical setting and are designed such that the patient's experience of having NAF collection is unacceptably distasteful or uncomfortable.

Patents and publications describing devices for the correction of inverted nipples or the collection of NAF fluid include: Pre-Grant Publications 2004/0176707, 2002/0072702, 2001/0031911, U.S. Pat. Nos. 6,712,785, 6,689,073, 6,500,112, 6,287,521, 6,210,360, 6,010,466, 5,871,456, 5,798,266, 5,947,923, 5,520,613, 3,786,801, 2,120,872, 1,922,947, 1,509,226, 897,289, 29,662 and 11,623; and WO's 03/017912 and 96/29043, British Patent Applications 2,325,411 and 2,240,924, and European Patent Application No. 0 442 758.

SUMMARY OF THE INVENTION

The present invention is an apparatus for treating inverted nipples and/or collecting NAF and a method of use thereof. An apparatus for treating inverted nipples in accordance with the invention is based upon a syringe body including a curved longitudinal axis which receives a syringe plunger with the plunger being moved along longitudinal axis curved around a chamber to draw a partial vacuum inside of the chamber into which an inverted nipple may project upon the application of partial vacuum or for the collection of NAF which is enhanced by the partial vacuum. The apparatus may be manufactured from different types of thermoplastics which without limitation are acceptable for application to the human body or plastics used in the manufacturing of syringes. The apparatus includes a cap which is rotatably attached to an outer surface of the chamber into which the inverted nipple may project or a nipple may project from which NAF is being collected. The cap carries the syringe plunger and upon rotation in a first direction, while the syringe plunger is received in the syringe body relative to the chamber, air is expelled from the syringe body away from the chamber and when an airtight seal exists between an attachment part and the breast surrounding the nipple rotation of the cap in a second direction moves the syringe plunger to produce a partial vacuum within the chamber. These two movements may be repeated to increase the partial vacuum within the chamber.

An apparatus for treating inverted nipples and/or collecting nipple aspirated fluids in accordance with the invention including a flexible attachment part including an opening, the attachment part being adapted for attachment to at least an areola of a nipple to create an airtight seal between the attachment part and the areola; a chamber extending away from the opening toward which the nipple may project upon application of a vacuum to the chamber while the attachment part is attached; a syringe plunger; a syringe body including a curved longitudinal axis which is curved around the chamber, the syringe body engaging an outer surface of the chamber, the syringe body including a first open end for receiving the syringe plunger which creates an airtight seal with an interior surface of the syringe body when received in the syringe body and a second end; a valve in fluid communication with the body, the syringe body being in fluid communication with the chamber, the valve opening to expel air away from the chamber upon movement of the syringe plunger within the syringe body toward the second end, movement of the syringe plunger within the syringe body away from the second end causing aspiration of air from the chamber to create a partial vacuum within the chamber when the attachment part is attached to the breast surrounding the nipple; and a cap rotatably attached to an outer surface of the chamber, the cap carrying the syringe plunger and rotation in a first direction while the syringe plunger is received in the syringe body causing air to be expelled from the syringe body through the valve and when an airtight seal exists between the attachment part and the breast surrounding the nipple air is rotation in a second direction moving the syringe plunger away from the second end to produce a partial vacuum within the chamber to apply an outward force to the nipple. These two movements may be repeated to increase the partial vacuum within the chamber. An absorbent material may be mounted within the chamber which upon contact with the nipple absorbs any nipple aspirate fluid; and include a biasing mechanism may be provided for biasing the absorbent material to contact the nipple which applies a force to the material to cause contact with the nipple while the apparatus is worn on the breast surrounding the nipple. The biasing mechanism may include a spring attached to an inner end of the cap and to a material holder which removably receives the material, the spring causing the material holder to cause contact of the material with the nipple. The cap may be removably and rotatably attached to a curved portion of an outer surface of the chamber; the fluid communication of the syringe body with the chamber may be through a conduit connecting the syringe body with an interior of the chamber; and a ratchet mechanism may be provided for rotatably stopping the cap relative to the chamber so that the syringe plunger is settable in different rotational positions relative to the chamber to set the partial vacuum upon rotation of the cap in the second direction. The attachment of the cap may comprise a periphery of a circular opening in the cap which slides within the curved portion. The attachment part may be coated with an adhesive which creates the airtight seal upon contact with the breast surrounding the nipple. The adhesive may be covered with a cover strip prior to use which is removed to expose the adhesive upon wearing of the apparatus so that the adhesive directly contacts the breast surrounding the nipple to create the airtight seal. An outer surface of the cap may include a gripping mechanism for gripping the cap so that a wearer of the apparatus may hold the gripping mechanism to facilitate rotation thereof upon attachment of the apparatus to the breast surrounding the nipple. The attachment may project away from an outer periphery thereof toward the opening to provide an inner surface of the attachment part for engaging the breast surrounding the nipple.

An apparatus for treating inverted nipples in accordance with the invention may include an assembly which creates an airtight seal upon attachment to at least an areola of an inverted nipple and which is activated by rotation of a part thereof to draw a partial vacuum to apply an outward force to the nipple; and a syringe including a curved longitudinal axis, the syringe being carried by the assembly and being in fluid communication with a chamber of the assembly upon attachment of the assembly to at least an areola of an inverted nipple, the syringe including a plunger which is sealed against an inner surface of the syringe and is rotatable to move along the longitudinal axis relative to the chamber which moves the plunger within a syringe body to expel air from the syringe body away from the chamber upon rotation of the plunger in a first direction and to aspirate air from the chamber upon attachment of the apparatus to the breast surrounding the nipple upon rotation in a second direction opposite to the first direction to create a partial vacuum within the chamber to evert the nipple. An absorbent material may be mounted within the chamber which upon contact with the nipple absorbs any nipple aspirate fluid; and include a biasing mechanism for biasing the absorbent material to contact the nipple which applies a force to the material to cause contact with the nipple while the apparatus is worn on the breast surrounding the nipple. The biasing mechanism may include a spring attached to an inner end of the cap and to a material holder which removably receives the material, the spring causing the material holder to cause contact of the material with the nipple. The cap may be removably and rotatably attached to a curved portion of an outer surface of the chamber; the fluid communication of the syringe body with the chamber may be through a conduit connecting the syringe body with an interior of the chamber; and a racket mechanism may be provided for rotatably stopping the cap relative to the chamber so that the syringe plunger is settable in different rotational positions relative to the chamber to set the partial vacuum upon rotation of the cap in the second direction. These two movements may be repeated to increase the partial vacuum within the chamber. The attachment of the cap may comprise a periphery of a circular opening in the cap which slides within the curved portion. The attachment part may be coated with an adhesive which creates the airtight seal upon contact with the breast surrounding the nipple. The adhesive may be covered with a cover strip prior to use which is removed to expose the adhesive upon wearing of the apparatus so that the adhesive directly contacts the breast surrounding the nipple to create the airtight seal. An outer surface of the cap may include a gripping mechanism for gripping the cap so that a wearer of the apparatus may hold the gripping mechanism to facilitate rotation thereof upon attachment of the apparatus to the breast surrounding the nipple. The attachment may project away from an outer periphery thereof toward the opening to provide an inner surface of the attachment part for engaging the breast surrounding the nipple.

A method of use of the apparatus as set forth above includes attaching the assembly to the breast surrounding the nipple of an inverted nipple with an airtight seal; and rotating the plunger within the syringe body to draw a partial vacuum within the chamber to apply a force to evert the inverted nipple.

A method of use of the apparatus as set forth above includes attaching the assembly to at least an areola of a nipple; rotating the plunger within the syringe body to draw a partial vacuum within the chamber to apply a force to evert the inverted nipple; and collecting nipple aspirate fluid by the material contacts the nipple.

DETAILED DESCRIPTION OF THE PREFERRED EMBODIMENT

Figure 1:
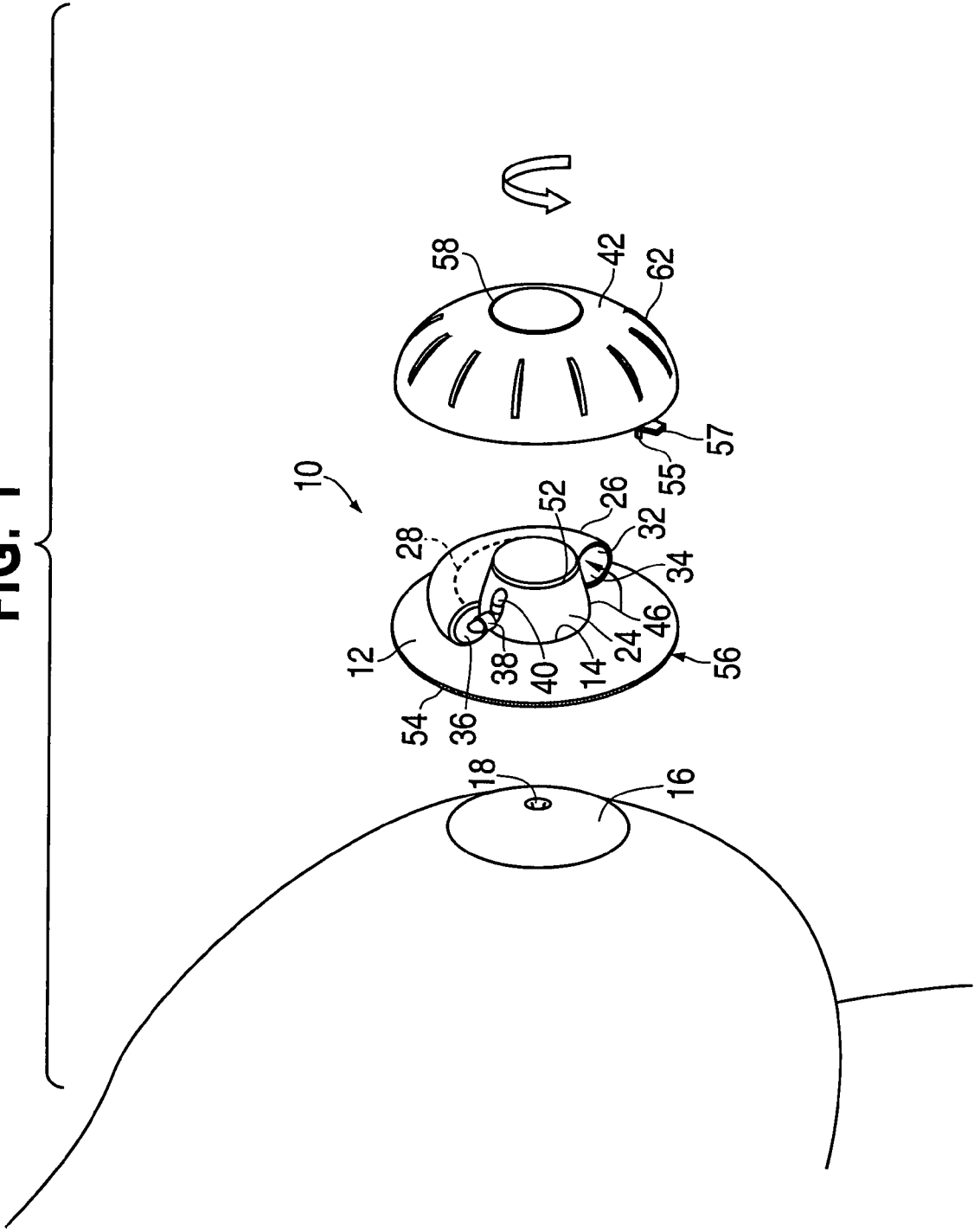
FIG. 1 illustrates an exploded view of an apparatus in accordance with the present invention positioned relative to a breast to be treated thereby with an inverted nipple.
Figure 2:
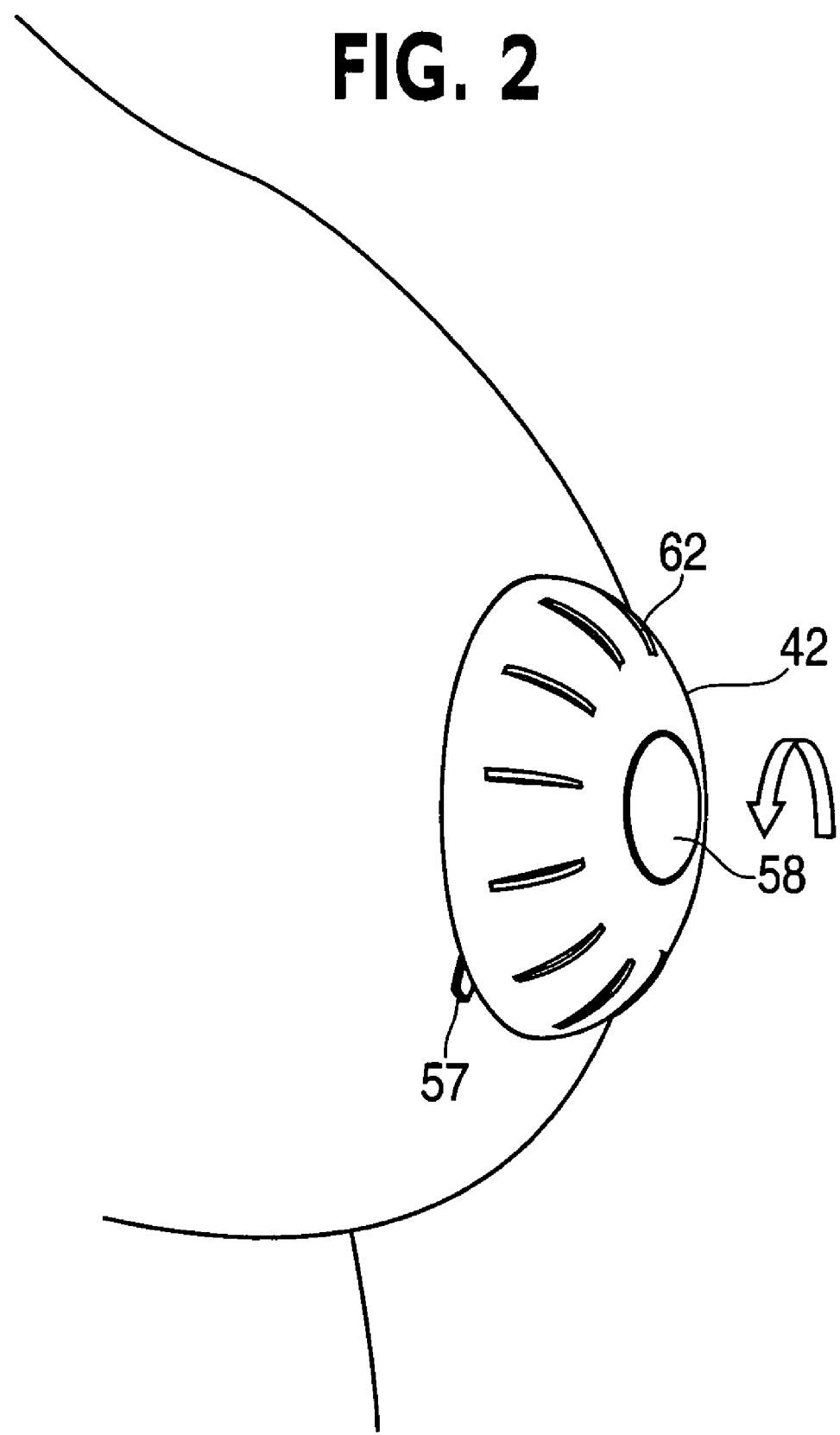
FIG. 2 is a view of the assembled invention positioned on the breast to treat the inverted nipple.
Figure 3:
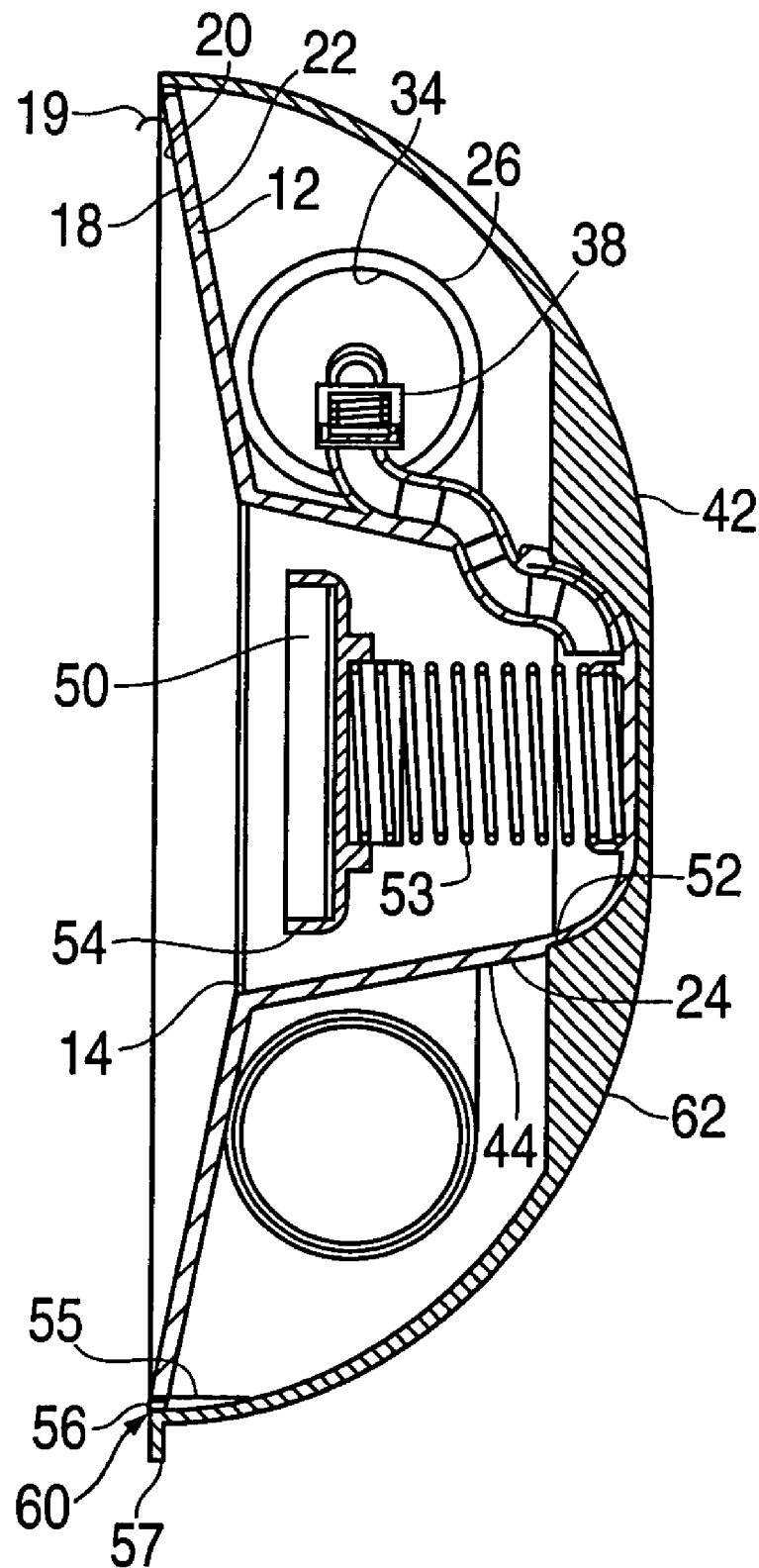
FIG. 3 is a sectional view of the assembled apparatus.
Figure 4:
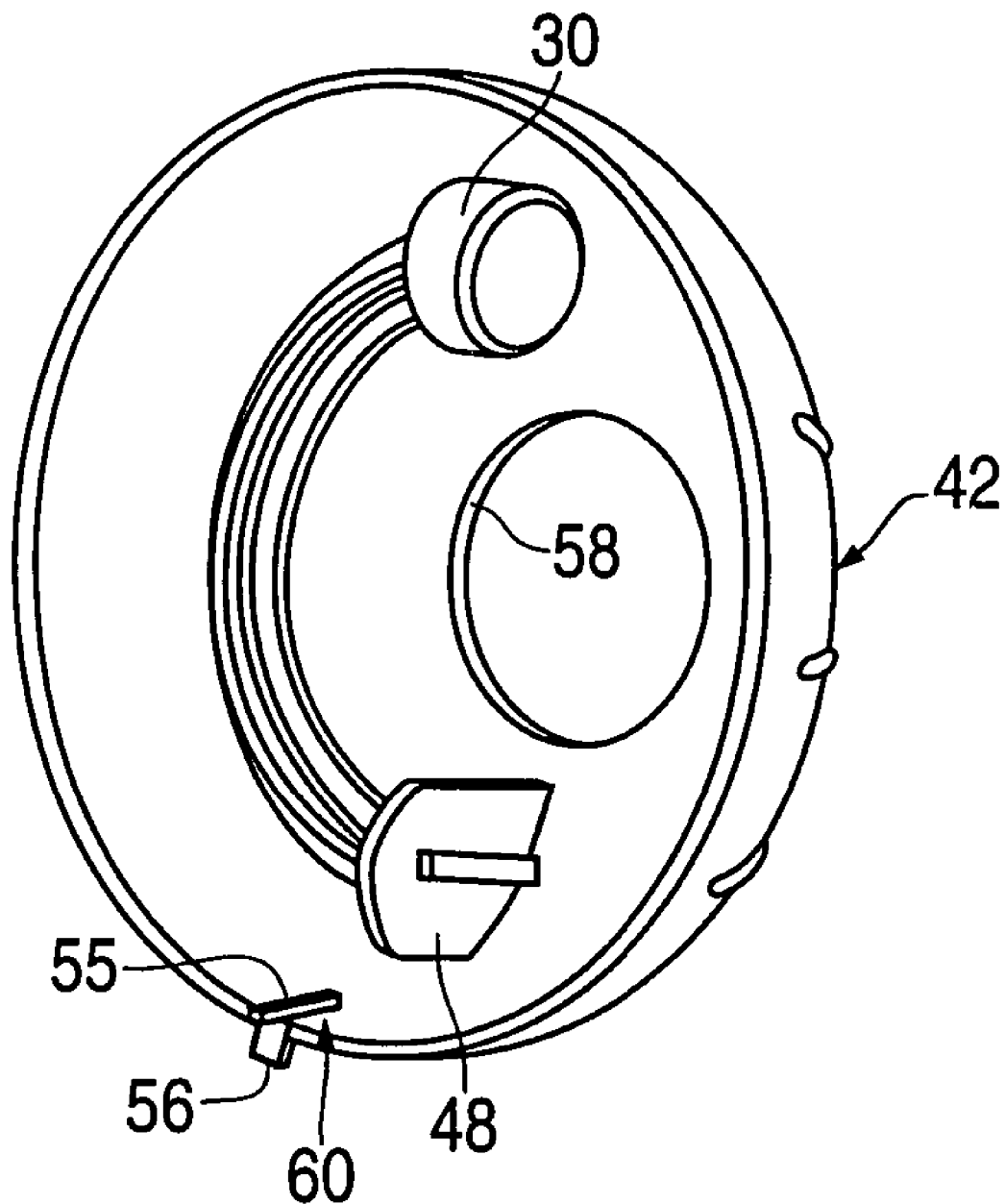
FIG. 4 is a view illustrating an interior of a rotatable of the present invention.

The present invention provides an apparatus for treating inverted nipples and/or collecting NAF and a method of use thereof. FIGS. 1-7 illustrate a preferred embodiment of the present invention. An apparatus 10 in accordance with the invention includes a flexible attachment part 12 including a central opening 14 from which a chamber 24 upwardly projects. The attachment part 12 is flexible to facilitate an inner surface by intimate contact with the breast surrounding the nipple 16 and covering the nipple 18 creating an airtight seal between the attachment part and the breast surrounding the nipple. A peel-away cover strip 19 covers adhesive layer 20 coated on the interior surface 22 of the flexible attachment part 12. The peel-away cover strip 19 is removed to expose the adhesive upon wearing of the apparatus by attachment to the breast surrounding the nipple 16 and covering the nipple 18 to create an airtight seal. An inverted nipple or a nipple during the collection of NAF projections into the chamber 24 upon application of a vacuum while the attachment part 12 is attached by the adhesive layer 20. A syringe 26, having a curved longitudinal axis 28, receives a syringe plunger 30 which rotates in first and second directions while contained within the syringe body to respectively expel air away from the chamber or draw a partial vacuum from the chamber. The syringe body 26 includes a first opening 32 for receiving the syringe plunger 30 which creates an airtight seal with an interior surface 34 of the syringe body when received in the syringe body and a second end 36. A valve 38 is in fluid communication with the syringe body 26 which may be mounted in a conduit 40 providing fluid communication with an interior of the syringe body and an interior of the chamber 24 so as to draw a partial vacuum from within the chamber when the syringe plunger 30 is moved in a second direction as indicated in FIG. 5C. The valve 38 opens to expel air away from the chamber upon movement of the syringe plunger in a first direction within the syringe body toward the second end 36 as illustrated in FIG. 5B. The circular movement of the syringe plunger 30 within the syringe body 26 in a second direction away from the second end 36 causes aspiration of the air from the interior of the chamber to create a partial vacuum within the chamber 24 when the attachment part 12 is attached to the breast surrounding the nipple 16. A cap 42 is rotatably attached into a channel 52 to an outer surface 46 of the chamber 24 or by any other well-known form or rotary connection. The cap 42 carries the syringe plunger on an interior surface as illustrated in FIG. 3 with a stop 48 being located at an opposite end of the circular travel of the syringe plunger 30 which limits the extension of the syringe plunger 30 into the syringe body 26. The plunger 30, upon rotation of the cap 42 relative to the chamber in the first direction, while the syringe plunger is received in the syringe body 26, causes the air to be expelled from the syringe body away from the chamber as illustrated in FIG. 5B through the valve 38. When an airtight seal exists between the attachment part 12 and the breast surrounding the nipple 16, air is aspirated from the interior of the chamber 24 into the syringe body 26 upon rotation of the cap 42 in the second direction to move the syringe plunger 30 away from the second end 36. The aspiration produces a partial vacuum within the chamber which applies an outward force to the nipple 18 to cause eversion thereof as illustrated in FIG. 6 or to promote collection of NAF from the nipple.

As illustrated in FIG. 3, an absorbent material 50, which is chosen to collect NAF and may be without limitation either woven or non-woven, is held in a holder 54 which is removably mounted by a snap fit or other mechanism into the top portion of the inside of the chamber within the chamber 24 which, upon contact with the nipple 18, absorbs any NAF. Treatment of inverted nipples is normally provided with the holder being removed as illustrated in FIG. 6. A biasing mechanism 53, which is preferably a plastic coil spring, causes the absorbent material 50 to contact the nipple 18 to facilitate the collection of NAF. Since the material 50 is absorbent, once the apparatus is removed from contact with the breast surrounding the nipple 16, the absorbent material may be removed from the material holder 54 to analyze any collected fluids thereon in accordance with well-known tests in the prior art. Parts 50, 53, and 54 may be held together by another mechanism which allows for ease of insertion and removal without contamination of the material holder 54.

Figure 5A:
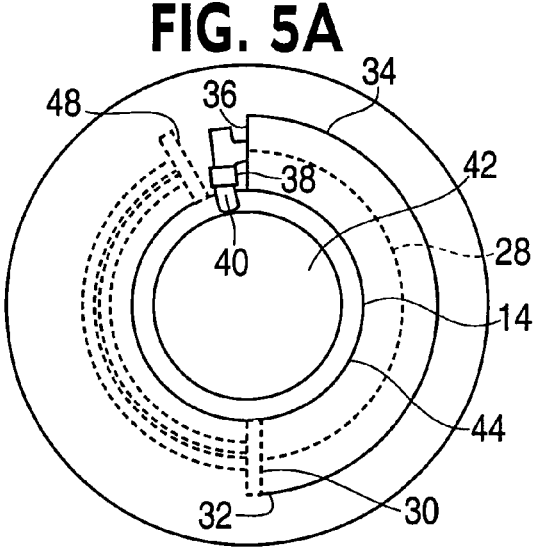
FIGS. 5A-5C are views illustrating the rotational deployment of the syringe plunger relative to the syringe body of the apparatus with the syringe plunger positioned at different points along the curved longitudinal axis of the syringe body illustrating operation of the present invention to drive air from the syringe body and draw partial vacuum inside of the chamber into which the inverted nipple is to drawn or NAF is to be drawn from a nipple.
Figure 5B:
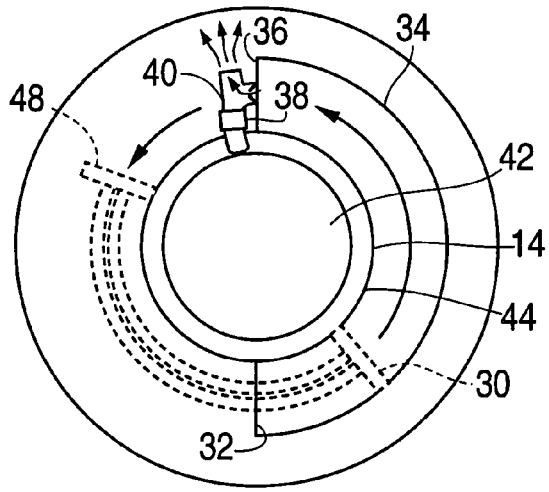
Figure 5C:
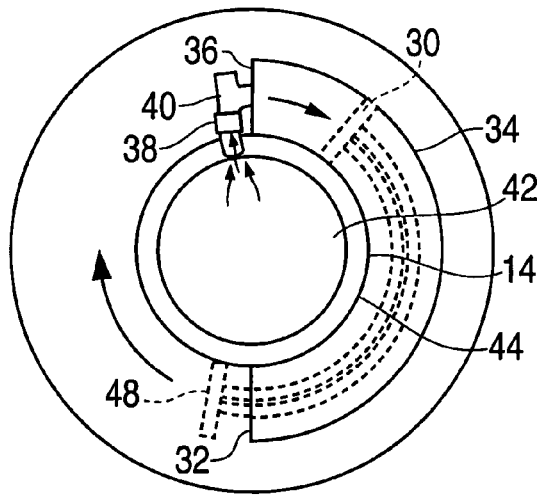
Figure 6:
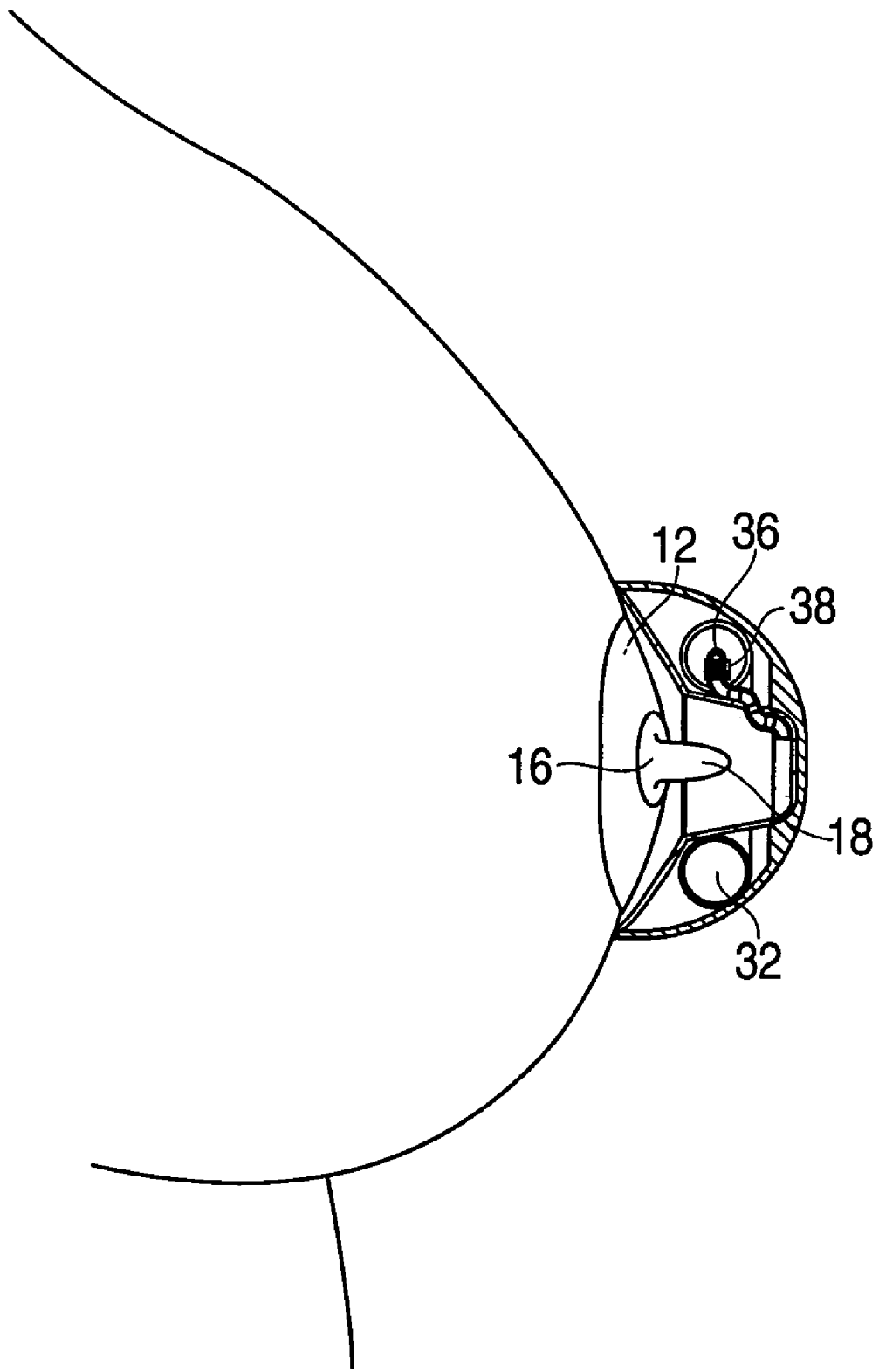
FIG. 6 illustrates the deployment of the present invention on a human breast after the application of partial vacuum within the chamber to cause the eversion of an inverted nipple with a NAF collection mechanism having been removed.

As may be seen from FIGS. 5A-5C, the operation of the present invention is based upon the attachment of the flexible attachment part 12 to the breast surrounding the nipple 16 by means of adhesive 20 which is exposed by peeling away the cover strip 19. If the rotatable cap 42 is not attached to the outside surface of the chamber 24, the cap is forced over the top of the outside surface 46 to engage the annular channel 52 cut in the outside surface of the chamber 24 to form a rotatable seal between the knob 42 and the outside surface of chamber. Thereafter, as illustrated in FIG. 5B, the plunger 30 is rotated counterclockwise to expel air from inside of the syringe body from the position as illustrated in FIG. 5A until the stop 48 contacts the first end 32 of the syringe body as illustrated generally in FIG. 5C. The clockwise rotation in FIG. 5C creates a partial vacuum within the interior of the chamber 24.

A two-way rotational stop or ratchet mechanism 60 locks the cap to a desired rotational position setting a desired partial vacuum. The stop or ratchet mechanism 60 may without limitation be at least one soft plastic tooth 55 carried on an interior surface of the cap 42 which engages teeth 54 of a circular gear 56 carried on an exterior surface of the attachment part. The at least one tooth 55 and gear teeth 54 of the circular gear 56 have a light engagement therebetween to permit the cap 42 to be rotated relative to the gear teeth without substantial force to cause the at least one tooth to selectively engage the teeth of the circular gear to permit rotation of the cap 42 to a desired setting for maintaining a set degree of partial vacuum which is dependent upon the position of the plunger 30 within the interior of the chamber. The at least one tooth 55 and the gear teeth 54 are made from flexible and elastic materials which have a limited degree of engagement permitting a relatively small application of rotational force applied by the fingers of the wearer to position the plunger 30 carried by the cap 42 to a rotational position somewhere between the second end 36 and the first end 32 to maintain a degree of partial vacuum which applies suction to the nipple 18 in order to apply outward force which is comfortable to the wearer or to facilitate collection of NAF. The tab 57 is attached to the outer surface of the cap 42 so as to permit lifting of the at least one tooth 55 carried by the interior of the cap 42 from engaging the corresponding teeth 54 of circular gear 56 so as to permit free rotation, releasing or applying the partial vacuum within the chamber 24 or to rotate the cap to a different position to vary the applied vacuum.

Figure 7:
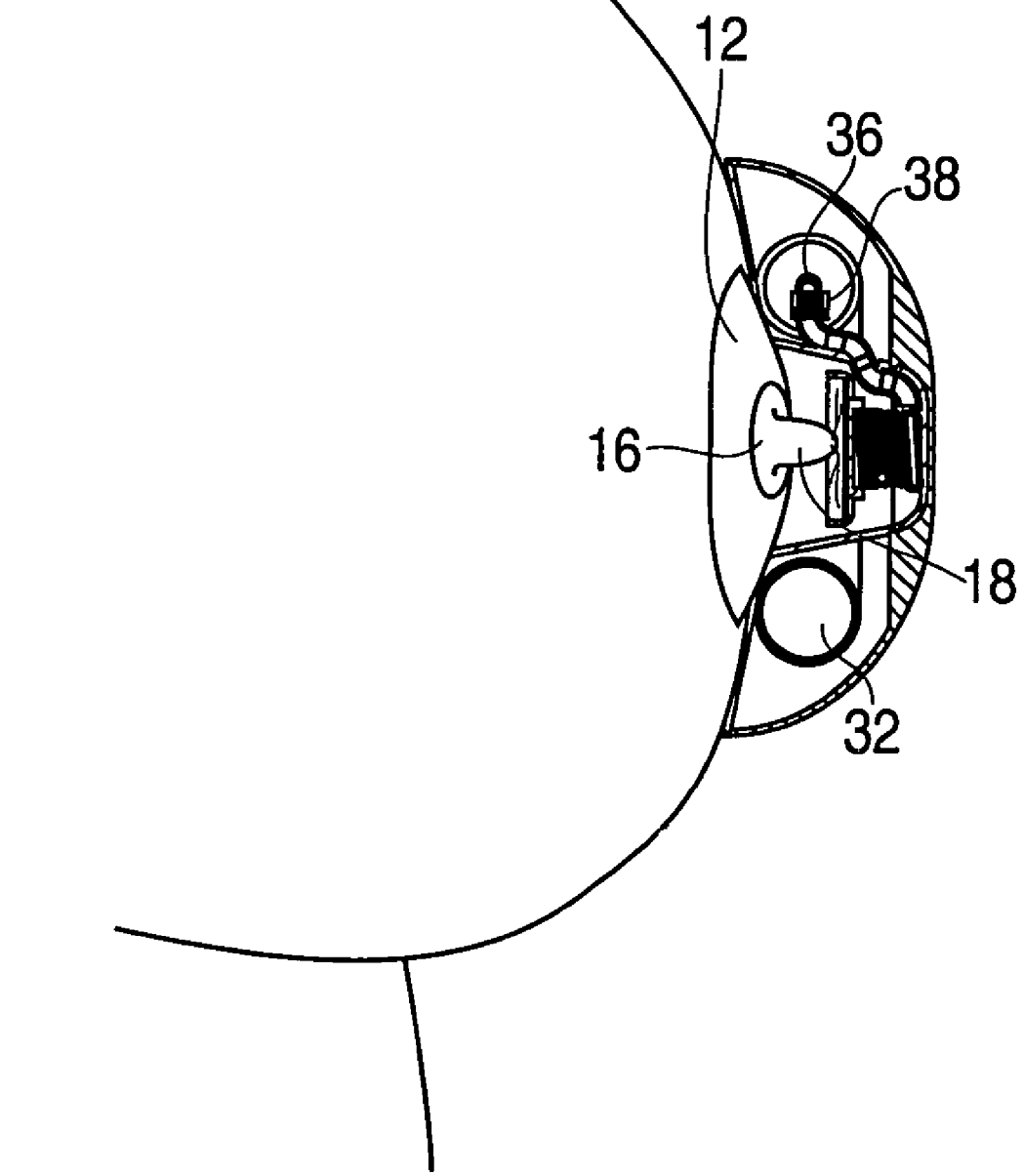
FIG. 7 illustrates the deployment of the present invention on a human breast after application of partial vacuum within the chamber with a NAF collection medium being deployed to contact the nipple.

The operation of the present invention to utilize the absorbent material 50 to collect NAF fluid is preferred in conjunction with a partial vacuum being applied to the areola 16 and nipple 18 but may be performed without the application of vacuum since the spring 52 will bias the material 50 against the nipple 18 as illustrated in FIG. 7. However, the application of vacuum to the inside of the chamber by the rotational positioning of the cap 42 may be used to apply a mild outward suction force to the nipple 18 to insure sufficient contact with the material 52 and the nipple while drawing fluid therefrom to permit the gathering of NAF fluid by suction.

In operation, the cap 42 is positioned such that the circular opening 58 rides within the channel 52 to form a rotatable attachment. It should be noted that FIGS. 3, 5A-5C and 6 do not illustrate the cap positioned over the top of the chamber 24, but in use, the cap 42 covers the syringe body 26 so it is not visible to the wearer.

The rotatable cap 42 may be removed and cleaned along with the attachment part 12 and chamber 24, which are preferably formed as a one-piece plastic structure such as, without limitation, the plastic from which syringes are made. Suitable commercial cleaning agents may be used since the materials from which these parts are made are preferably plastic which is highly stable against damage by the use of cleaning agents.

A gripping mechanism 62 is provided on the outside surface of the rotatable cap 42 to permit the wearer of the apparatus to grip the cap 42 to facilitate rotation of the rotatable cap relative to the underlying attachment part 12 and chamber 24 so as to choose the degree of vacuum to be used for treating of an inverted nipple or the collecting of NAF fluid.

The attachment part 12 is designed to conform to the natural shape of the breast and can be comfortably worn under clothing or during sleeping. The apparatus most effectively is used to aspirate NAF fluid by the gentle and constant application of negative pressure to the nipple. The collected volume of NAF fluid is highly variable among women depending on several factors including the women's physiology, whether or not she has been pregnant, has breast fed children, or the stage of her menstrual cycle when the sample is collected. The collection of NAF fluid may be in combination with several techniques also implemented by the patient which may increase the volume of NAF fluid collected. These techniques include an application of a material, such as alcohol or Cerumux which dissolves any carotene plugs which typically form on the outlets of the lactiferous ducts, intranasal administration of oxytocin to promote expulsion of NAF from the milk ducts, wearing the collection device at night when parasympathetic stimulation of the mammary glands would be expected to be elevated promoting NAF formation, massage of the breast during aspiration and pulling of samples over several collection trials.

Moreover, based on a well observed phenomena that breast feeding exerts a protective effect against breast cancer combined with the observation that in samples of serially obtained NAF, the latter samples contain lower levels of carcinogenic materials, some researchers have proposed that periodic flushing of the lactiferous ducts in non-lactating women might also be some protection against the development of breast cancer. The present invention may be used for screening large numbers of women involved with the periodic flushing of the lactiferous duct system.

The attachment part 12 is light and flexible where contact with the breast surrounding the nipple 16 of the patient occurs. The attachment part 12 is desirably more flexible than the chamber 24. The chamber 24 should be at least somewhat rigid in order to maintain a negative pressure to provide a good seal and to optimize sample collection. The attachment part 12 may be made of clear plastic to make the chamber 24 interior visible to an observer. The rotatable cap 42 is ergonomically designed for ease of grip and its profile will be minimized to allow the highest comfort possible should this device be used during sleeping. The overall dimensions of the invention may be scaled up or down in order to accommodate various breast sizes and shapes.

The use of the present invention is simple with the attachment part being placed on the patient after the adhesive strip 19 is exposed followed by a 90-180° turn of the cap to expel the air from the interior of the syringe 32 and to thereafter draw at least a partial vacuum from the chamber 24. Once the cap 42 is positioned, the stop or ratchet mechanism 60 keeps the cap from slipping, thus maintaining the desired partial vacuum. The tab 57 is used to release the cap 42 by lifting the at least one tooth away from the teeth 54 of the attachment part 12 to prevent accidental release. The tab 57 also allows the cap 42 to be separated from engagement of the channel 52 in the exterior surface of the chamber 24. The material 50 uses simple absorption or capillary action to collect and hold NAF. The material 50 preferably has perforations in the disks which are sized to accommodate the high viscosity of NAF with the disk being held in place in contact with the nipple 18 by the spring 52. The spring 52 holds the material 50 against the nipple 18 insuring that all NAF fluid is collected either in a fluid reservoir within the interior of the chamber or within the material minimizing the waste of sample. The material holder 54 retains the material 50 so that the disk remains in place in the holder should the apparatus be taken off intentionally or accidentally. The material holder 54 may be removed when the invention is used only for the treatment of inverted nipples.

While the invention has been described in terms of its preferred embodiment, numerous modifications may be made thereto without departing from the spirit and scope of the present invention. It is intended that all such modifications fall within the scope of the appended claims.

The invention claimed is:

1. An apparatus for treating inverted nipples and/or collecting nipple aspirate fluids comprising:
    a flexible attachment part including an opening, the attachment part being adapted for attachment to at least an areola of a nipple to create an airtight seal between the attachment part and the areola;
    a chamber extending away from the opening toward which the nipple may project upon application of a vacuum to the chamber while the attachment part is attached;
    a syringe plunger;
    a syringe body including a curved longitudinal axis which is curved around the chamber, the syringe body engaging an outer surface of the chamber, the syringe body including a first open end for receiving the syringe plunger which creates an airtight seal with an interior surface of the syringe body when received in the syringe body and a second end;
    a valve in fluid communication with the body, the syringe body being in fluid communication with the chamber, the valve opening to expel air away from the chamber upon movement of the syringe plunger within the syringe body toward the second end, movement of the syringe plunger within the syringe body away from the second end causing aspiration of air from the chamber to create a partial vacuum within the chamber when the attachment part is attached at least to the areola; and
    a cap rotatably attached to an outer surface of the chamber, the cap carrying the syringe plunger and rotation in a first direction while the syringe plunger is received in the syringe body causing air to be expelled from the syringe body through the valve and when an airtight seal exists between the attachment part and the breast surrounding the nipple air is rotation in a second direction moving the syringe plunger away from the second end to produce a partial vacuum within the chamber to apply an outward force to the nipple.

2. An apparatus in accordance with claim 1 comprising:
    an absorbent material mounted within the chamber which upon contact with the nipple absorbs any nipple aspirate fluid; and a biasing mechanism for biasing the absorbent material to contact the nipple which applies a force to the material to cause contact with the nipple while the apparatus is worn on the breast surrounding the nipple.

3. An apparatus in accordance with claim 2 wherein the biasing mechanism includes a spring attached to an inner end of the cap and to a material holder which removably receives the material, the spring causing the material holder to cause contact of the material with the nipple.

4. An apparatus in accordance with claim 1 comprising:
means for removably and rotatably attaching the cap to a curved portion of an outer surface of the chamber;
the fluid communication of the syringe body with the chamber being through a conduit connecting the syringe body with an interior of the chamber; and
a racket mechanism for rotatably stopping the cap relative to the chamber so that the syringe plunger is settable in different rotational positions relative to the chamber to set the partial vacuum upon rotation of the cap in the second direction.

5. An apparatus in accordance with claim 4 wherein the means comprises a periphery of a circular opening in the cap which slides within the curved portion.

6. An apparatus in accordance with claim 2 comprising:
means for removably and rotatably attaching the cap to a curved portion of an outer surface of the chamber;
the fluid communication of the syringe body with the chamber being through a conduit connecting the syringe body with an interior of the chamber; and
a racket mechanism for rotatably stopping the cap relative to the chamber so that the syringe plunger is settable in different rotational positions relative to the chamber to set the partial vacuum upon rotation of the cap in the second direction.

7. An apparatus in accordance with claim 6 wherein the means comprise a periphery of a circular opening in the cap which slides within the curved portion.

8. An apparatus in accordance with claim 3 comprising:
means for removably and rotatably attaching the cap to a curved portion of an outer surface of the chamber;
the fluid communication of the syringe body with the chamber being through a conduit connecting the syringe body with an interior of the chamber; and
a racket mechanism for rotatably stopping the cap relative to the chamber so that the syringe plunger is settable in different rotational positions relative to the chamber to set the partial vacuum upon rotation of the cap in the second direction.

9. An apparatus in accordance with claim 4 wherein the means comprises a periphery of a circular opening in the cap which slides within the curved portion.

10. An apparatus in accordance with claim 1 wherein the curved longitudinal axis of the syringe body extends partially around an outside surface of the chamber.

11. An apparatus in accordance with claim 1 wherein the attachment part is coated with an adhesive which creates the airtight seal upon contact with the breast surrounding the nipple.

12. An apparatus in accordance with claim 11 wherein the adhesive is covered with a cover strip prior to use which is removed to expose the adhesive upon wearing of the apparatus so that the adhesive directly contacts the breast surrounding the nipple to create the airtight seal.

13. An apparatus in accordance with claim 1 wherein:
an outer surface of the cap includes a gripping mechanism for gripping the cap so that a wearer of the apparatus may hold the gripping mechanism to facilitate rotation thereof upon attachment of the apparatus to the breast surrounding the nipple.

14. An apparatus in accordance with claim 1 wherein the attachment part projects away from an outer periphery thereof toward the opening to provide an inner surface of the ring for engaging the breast surrounding the nipple.

15. An apparatus in accordance with claim 2 wherein the attachment part projects away from an outer periphery thereof toward the opening to provide an inner surface of the ring for engaging the breast surrounding the nipple.

16. An apparatus in accordance with claim 3 wherein the attachment part projects away from an outer periphery thereof toward the opening to provide an inner surface of the ring for engaging the breast surrounding the nipple.

17. An apparatus in accordance with claim 4 wherein the attachment part projects away from an outer periphery thereof toward the opening to provide an inner surface of the ring for engaging the breast surrounding the nipple.

18. An apparatus in accordance with claim 5 wherein the attachment part projects away from an outer periphery thereof toward the opening to provide an inner surface of the ring for engaging the breast surrounding the nipple.

19. An apparatus in accordance with claim 6 wherein the attachment part projects away from an outer periphery thereof toward the opening to provide an inner surface of the ring for engaging the breast surrounding the nipple.

20. An apparatus in accordance with claim 7 wherein the attachment part projects away from an outer periphery thereof toward the opening to provide an inner surface of the ring for engaging the breast surrounding the nipple.

21. An apparatus in accordance with claim 8 wherein the attachment part projects away from an outer periphery thereof toward the opening to provide an inner surface of the ring for engaging the breast surrounding the nipple.

22. An apparatus in accordance with claim 9 wherein the attachment part projects away from an outer periphery thereof toward the opening to provide an inner surface of the ring for engaging the breast surrounding the nipple.

23. An apparatus in accordance with claim 10 wherein the attachment part projects away from an outer periphery thereof toward the opening to provide an inner surface of the ring for engaging the breast surrounding the nipple.

24. An apparatus in accordance with claim 11 wherein the attachment part projects away from an outer periphery thereof toward the opening to provide an inner surface of the ring for engaging the breast surrounding the nipple.

25. An apparatus in accordance with claim 12 wherein the attachment part projects away from an outer periphery thereof toward the opening to provide an inner surface of the ring for engaging the breast surrounding the nipple.

26. An apparatus in accordance with claim 13 wherein the attachment part projects away from an outer periphery thereof toward the opening to provide an inner surface of the ring for engaging the breast surrounding the nipple.

27. An apparatus for treating inverted nipples comprising:
an assembly which creates an airtight seal upon attachment to the breast surrounding the nipple of an inverted nipple and which is activated by rotation of a part thereof to draw a partial vacuum to apply an outward force to the nipple; and
a syringe including a curved longitudinal axis, the syringe being carried by the assembly and being in fluid communication with a chamber of the assembly upon attachment of the assembly to at least an areola of an inverted nipple, the syringe including a plunger which is sealed against an inner surface of the syringe and is rotatable to move along the longitudinal axis relative to the chamber which moves the plunger within a syringe body to expel air from the syringe body away from the chamber upon rotation of the plunger in a first direction and to aspirate air from the chamber upon attachment of the apparatus to the breast surrounding the nipple and upon rotation in a second direction opposite to the first direction to create a partial vacuum within the chamber to evert the nipple.

28. An apparatus in accordance with claim 27 comprising:
an absorbent material mounted within the chamber which upon contact with the nipple absorbs any nipple aspirate fluid; and
a biasing mechanism for biasing the absorbent material to contact the nipple which applies a force to the material to cause contact with the nipple while the apparatus is worn on the breast surrounding the nipple.

29. An apparatus in accordance with claim 28 wherein the biasing mechanism includes a spring attached to an inner end of the cap and to a material holder which removably receives the material, the spring causing the material holder to cause contact of the material with the nipple.

30. An apparatus in accordance with claim 27 comprising:
means for removably and rotatably attaching the cap to a curved portion of an outer surface of the chamber;
the fluid communication of the syringe body with the chamber being through a conduit connecting the syringe body with an interior of the chamber; and
a racket mechanism for rotatably stopping the cap relative to the chamber so that the syringe plunger is settable in different rotational positions relative to the chamber to set the partial vacuum upon rotation of the cap in the second direction.

31. An apparatus in accordance with claim 30 wherein the means comprises
a periphery of a circular opening in the cap which slides within the curved portion.

32. An apparatus in accordance with claim 27 wherein the curved longitudinal axis of the syringe body extends partially around an outside surface of the chamber.

33. An apparatus in accordance with claim 27 wherein the attachment part is coated with an adhesive which creates the airtight seal upon contact with the breast surrounding the nipple.

34. An apparatus in accordance with claim 33 wherein the adhesive is covered with a cover strip prior to use which is removed to expose the adhesive upon wearing of the apparatus so that the adhesive directly contacts the breast surrounding the nipple to create the airtight seal.

35. An apparatus in accordance with claim 27 wherein:
an outer surface of the cap includes a griping mechanism for gripping the cap so that a wearer of the apparatus may hold the gripping mechanism to facilitate rotation thereof upon attachment of the apparatus to the breast surrounding the nipple.

36. An apparatus in accordance with claim 27 wherein the attachment part projects away from an outer periphery thereof toward the opening to provide an inner surface of the ring for engaging the breast surrounding the nipple.

37. A method of use of the apparatus of claim 27 comprising:
attaching the assembly to the breast surrounding the nipple of an inverted nipple with an airtight seal; and
rotating the plunger within the syringe body to draw a partial vacuum within the chamber to apply a force to evert the inverted nipple.

38. A method of use of the apparatus of claim 28 comprising:
attaching the assembly to at least an areola of a nipple;
rotating the plunger within the syringe body to draw a partial vacuum within the chamber to apply a force to evert the inverted nipple; and
collecting nipple aspirate fluid by the material contacting the nipple.

* * * * *